(12) United States Patent
Chotchatchawankul et al.

(10) Patent No.: US 11,179,709 B2
(45) Date of Patent: Nov. 23, 2021

(54) CATALYST COMPOSITION FOR A PRODUCTION PROCESS OF δ-LACTONE FROM CARBON DIOXIDE AND 1,3-BUTADIENE

(71) Applicant: PTT GLOBAL CHEMICAL PUBLIC COMPANY LIMITED, Bangkok (TH)

(72) Inventors: Sucheewin Chotchatchawankul, Rayong (TH); Phonpimon Wongmahasirikun, Rayong (TH); Sophon Kaeothip, Bangkok (TH); Khamphee Phomphrai, Rayong (TH)

(73) Assignee: PTT GLOBAL CHEMICAL PUBLIC COMPANY LIMITED, Bangkok (TH)

( * ) Notice: Subject to any disclaimer, the term of this patent is extended or adjusted under 35 U.S.C. 154(b) by 245 days.

(21) Appl. No.: 16/474,615

(22) PCT Filed: Nov. 8, 2017

(86) PCT No.: PCT/TH2017/000080
§ 371 (c)(1),
(2) Date: Jun. 28, 2019

(87) PCT Pub. No.: WO2018/124978
PCT Pub. Date: Jul. 5, 2018

(65) Prior Publication Data
US 2019/0321813 A1    Oct. 24, 2019

(30) Foreign Application Priority Data
Dec. 28, 2016   (TH) .................... 1601007808

(51) Int. Cl.
C07D 309/30   (2006.01)
B01J 31/22    (2006.01)

(52) U.S. Cl.
CPC ........ B01J 31/2213 (2013.01); C07D 309/30 (2013.01)

(58) Field of Classification Search
None
See application file for complete search history.

(56) References Cited

PUBLICATIONS

Dey et al Journal of the Indian Chemical Society, 49, 9, 907-8) (Year: 1972).*

* cited by examiner

Primary Examiner — Yun Qian
(74) Attorney, Agent, or Firm — Culhane Meadows, PLLC

(57) ABSTRACT

This present invention relates to a catalyst composition for a production process of δ-lactone from carbon dioxide and 1,3-butadiene that can efficiently catalyze the synthesis reaction of δ-lactone with good selectivity of δ-lactone, wherein said catalyst composition comprising: a) palladium metal complexes as shown in structure (I) [Formula should be inserted here] wherein, $R^1$, $R^2$, $R^3$ and $R^4$ independently represents a group selected from a hydrogen atom, a halogen atom, an alkyl group, an alkoxy group, an amine group, or optionally an alkenyl group, an alkynyl group, a phenyl group, a benzyl group, or a cyclic hydrocarbon group comprising a hetero atom; and b) phosphorus compound selected from a phosphine group having a general formula [Formula should be inserted here], wherein $R^5$ is selected from an alkyl group, a cycloalkyl group, or an aryl group.

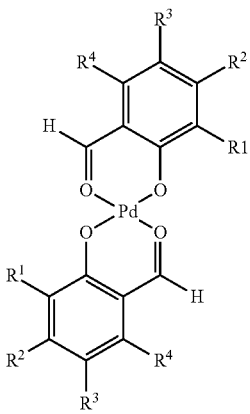

16 Claims, No Drawings

CATALYST COMPOSITION FOR A PRODUCTION PROCESS OF δ-LACTONE FROM CARBON DIOXIDE AND 1,3-BUTADIENE

TECHNICAL FIELD

Science relates to a catalyst composition for a production process of δ-lactone from carbon dioxide and olefin.

BACKGROUND OF THE INVENTION

Carbon dioxide gas is one of the greenhouse gases generated from combustion in many industries such as coal, cement, and electricity industries, including petroleum and petrochemical industries. Although carbon dioxide gas is low toxic, the carbon dioxide gas released in abundant amount creating the greenhouse effect which increasing earth surface temperature.

Nevertheless, the carbon dioxide gas is the renewable resource. Moreover carbon dioxide gas is used as $C_1$ building block in the production of costly chemical such as urea, salicylic acid, cyclic carbonate and lactone, etc. However, the main problem of the utilization of the carbon dioxide gas is the inert chemical property of the carbon dioxide gas. Therefore, the reaction with the high reactivity substance or the use of catalyst in order to transform carbon dioxide gas into the desired chemicals is required.

Lactone is the interested cyclic ester group because it can be used as the precursor for the synthesis of polyester. It is also the precursor for the production of many other costly derivatives. The synthesis of lactone from carbon dioxide can be done by the telomerization of carbon dioxide with small olefins using a catalyst.

Journal of the Chemical Society, Chemical Communications (1976) and Bulletin of the Chemical Society of Japan (1978) disclose the synthesis of γ-lactone from the reaction of carbon dioxide and 1,3-butadiene in dimethylformamide solvent using Pd-diphosphine complex as the catalyst. It was found that the lactone could be synthesized up to 12.3% comparing with the starting 1,3-butadiene at the selectivity of 15%.

Inorganica Chimica Acta (1978), Journal of the Chemical Society, Perkin Transactions 1 (1980), and U.S. Pat. No. 4,167,513 disclose the use of Pd-monophosphine complex as the catalyst and a non-polar solvent such as benzene in the synthesis of δ-lactone.

U.S. Pat. No. 4,393,224 discloses the synthesis process of δ-lactone from the reaction of carbon dioxide gas and 1,3-butadiene using palladium phosphine complex tertiary amine and quinone or hydroquinone compound as the catalytic system. The said reaction had selectivity of δ-lactone of 89%.

Synthesis (1983) and EP 0124725A1 disclose the synthesis of δ-lactone from carbon dioxide and 1,3-butadiene using palladium complex with the oxidation number of 2, (Pd(II)) and β-dicarbonyl ligand such as acetylacetonate, allyl or diene, and biscarboxylate together with phosphine ligand as the catalyst.

Journal of the American Chemical Society (1988) and FR 2617163 disclose the use of cationic palladium complex as the catalyst, wherein ligand was in the group of phosphine compound or nitrile or halide for the production of δ-lactone.

Moreover, Journal of Molecular Catalysis A: Chemical (1997) discloses the use of phosphine ligand having a nitrile group as the catalyst for the synthesis reaction of δ-lactone together with palladium complex in organic solvent. The selectivity of δ-lactone was 74%.

In the same way, Journal of Organometallic Chemistry (2012) discloses the synthesis of δ-lactone by the palladium complex with the bidentate ligand as the tertiary amine phosphine in the acetonitrile solvent. The said complex could provide up to 60% yield at the selectivity of 79%. Tetrahedron Letters (2016) and CN 105622560 disclose the palladium nanoparticles and quaternary ammonium salts under a ligand-free condition. It was found that the said catalyst provided 51% δ-lactone product with selectivity of 94%.

However, the catalysts for the synthesis of δ-lactone by the reaction of carbon dioxide and 1,3-butadiene as disclosed are limited to the palladium complex and phosphine, β-dicarbonyl, allyl or diene, carboxylate, amine, nitrile, or dibenzylideneacetone ligands only. The disclosure of the structural improvement of the said compounds in order to develop the catalytic activity is not found. Moreover, the basic structure of the ligand is limited in both electronic and steric properties.

From these reasons, this invention aims to develop the efficacy of the catalytic system for the synthesis of δ-lactone by the reaction of carbon dioxide and 1,3-butadiene. The said catalyst composition comprises palladium complex and salicylaldehyde ligand including its derivatives and phosphorus phosphine group as the catalyst, which is easy to be synthesized, stable to air and humidity, and capable to efficiently catalyze the synthesis reaction of δ-lactone with good selectivity to δ-lactone.

SUMMARY OF INVENTION

This present invention relates to the catalyst composition for a production process of δ-lactone from carbon dioxide and 1,3-butadiene that can efficiently catalyze the synthesis reaction of δ-lactone with a good selectivity of δ-lactone, wherein said catalyst composition comprising:

a) palladium metal complexes as shown in structure (I)

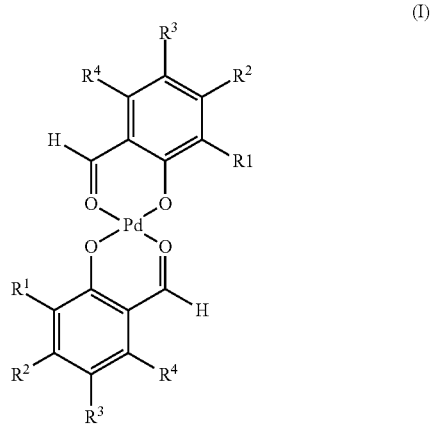

wherein, $R^1$, $R^2$, $R^3$ and $R^4$ independently represents a group selected from a hydrogen atom, a halogen atom, an alkyl group, an alkoxy group, an amine group, or optionally an alkenyl group, an alkynyl group, a phenyl group, a benzyl group, or a cyclic hydrocarbon comprising a hetero atom; and b) phosphorus compound selected from a phosphine group having a general formula $PR_3^5$, wherein $R^5$ is selected from an alkyl group, a cycloalkyl group, or aryl group.

DESCRIPTION OF THE INVENTION

This present invention relates to the catalyst composition for a production process of δ-lactone from carbon dioxide and 1,3-butadiene, wherein the catalyst according to the invention can be efficiently catalyze the synthesis reaction of δ-lactone with a good selectivity to δ-lactone. Moreover, the catalyst according to the invention is easy to be synthesized and stable to air and humidity. The catalyst according to the invention can be described according to the following detailed description.

Any aspect being shown herein refers including its application to the other aspects of this invention unless stated otherwise.

Technical terms or scientific terms used herein have definitions as understood by an ordinary person skilled in the art unless stated otherwise.

Any tools, equipment, methods, or chemicals mentioned here mean tools, equipment, methods, or chemicals commonly operated or use by those person skilled in the art unless explicated that they are tools, equipment, methods, or chemicals specific only in this invention.

Use of singular noun or singular pronoun with "comprising" in claims or specification refers to "one" and also "one or more", "at least one", and "one or more than one".

All compositions and/or methods disclosed and claimed in this application aim to cover the embodiments from any action, performance, modification, or adjustment without any experiment that significantly different from this invention, and obtained with the objection of utility and resulted as same as the present embodiment according to a person ordinary skilled in the art although without specifically stated in claims. Therefore, substitutable or similar object to the present embodiment, including any little modification or adjustment that clearly seen by person skilled in the art should be construed as remains in spirit, scope, and concept of invention as appeared in appended claims.

Throughout this application, term "about" means any number that appeared or showed here that could be varied or deviated from any error of equipment, method, or personal using said equipment or method including variation or deviation caused from changes in physical properties.

Hereafter, the invention of this embodiments are shown without any purpose to limit any scope of the invention.

This invention relates to the catalyst composition for a production process of δ-lactone from carbon dioxide and 1,3-butadiene that can efficiently catalyze the synthesis reaction of δ-lactone with the good selectivity of δ-lactone, wherein said catalyst composition comprising:

a) palladium metal complexes as shown in structure (I)

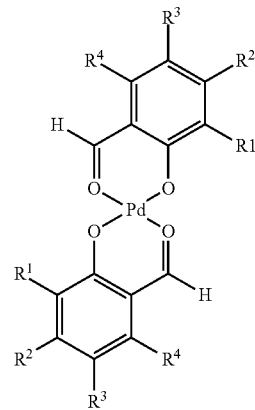

(I)

wherein, $R^1$, $R^2$, $R^3$ and $R^4$ independently represents a group selected from a hydrogen atom, a halogen atom, an alkyl group, an alkoxy group, an amine group, or optionally an alkenyl group, an alkynyl group, a phenyl group, a benzyl group, or a cyclic hydrocarbon comprising hetero atom; and b) a phosphorus compound selected from a phosphine group with a general formula $PR_3^5$, wherein $R^5$ is selected from an alkyl group, a cycloalkyl group, or an aryl group.

In one embodiment, the palladium metal complexes in a), $R^1$, $R^2$, $R^3$ and $R^4$ independently represents groups selected from a hydrogen atom, a halogen atom, an alkyl having 1-4 carbon atoms, an alkoxy having 1-4 carbon atoms, or a secondary amine having a general formula $NR^6$, wherein $R^6$ is an alkyl having 1-4 carbon atoms.

In one embodiment, the palladium metal complexes in a), $R^1$, $R^2$, $R^3$ and $R^4$ independently represents group selected from, but not limited to a hydrogen atom, a chlorine atom, a bromine atom, a methyl atom, an ethyl atom, an isopropyl atom, a n-butyl atom, a tert-butyl atom, a methoxy atom, an ethoxy atom, an iso-propoxy atom, a n-butoxy atom, a tert-butoxy atom, a dimethylamine atom, a diethylamine atom, a di-n-butylamine atom.

In one embodiment, the palladium metal complexes in a) may be selected from, but not limited to palladium (II) salicylaldehyde, palladium (II) methoxy salicylaldehyde, palladium (II) 4-methoxy salicylaldehyde, palladium (II) 5-methoxy salicylaldehyde, palladium (II) 4,6-dimethoxy salicylaldehyde, palladium (II) 4-diethylamino salicylaldehyde, palladium (II) 4-dibutylamino salicylaldehyde, palladium (II) 5-bromo salicylaldehyde, palladium (II) 5-chloro salicylaldehyde, palladium (II) 3,5-dichloro salicylaldehyde, palladium (II) 3-methyl salicylaldehyde, palladium (II) 4-methyl salicylaldehyde, and palladium (II) 5-methyl salicylaldehyde.

Preferably, the palladium metal complexes in a) is selected from palladium (II) salicylaldehyde, palladium (II) 4,6-dimethoxy salicylaldehyde, palladium (II) 4-diethylamino salicylaldehyde, palladium (II) 4-dibutylamino salicylaldehyde, palladium (II) 5-chloro salicylaldehyde, and palladium (11) 3,5-dichloro salicylaldehyde.

In one embodiment, the palladium metal complexes in a) can be synthesized from the reaction of palladium metal salt and a group of salicylaldehyde ligand and its derivatives under pH condition about 5-8, wherein the mole ratio in the reaction of palladium to ligand is in a range of 3:1 to 1:3.

In one embodiment, the palladium metal salt precursor can be selected from, but not limited to palladium chloride ($PdCl_2$), palladium bromide ($PdBr_2$), palladium trifluoroacetate ($Pd(TFA)_2$) or palladium acetate ($Pd(OAc)_2$). Preferably, the palladium metal salt precursor is palladium chloride.

In another embodiment of the invention, the salicylaldehyde ligand and its derivatives can be selected from, but not limited to salicylaldehyde, 3-methoxy salicylaldehyde, 4-methoxy salicylaldehyde, 5-methoxy salicylaldehyde, 4,6-dimethoxy salicylaldehyde, 4-diethylamino salicylaldehyde, 4-dibutylamino salicylaldehyde, 5-bromo salicylaldehyde, 5-chloro salicylaldehyde, 3,5-dichloro salicylaldehyde, 3-methyl salicylaldehyde, 4-methyl salicylaldehyde, and 5-methyl salicylaldehyde.

In one embodiment, the phosphorus compound in b) is selected from, but not limited to triphenylphosphine, tricyclohexylphosphine, tris(2-methoxyphenyl)phosphine, tris(4-methoxyphenyl)phosphine), or mixture thereof. Preferably, the phosphorus compound in b) is selected from triphenylphosphine.

In one embodiment, the ratio of composition a) and b) is in a range of 1:1 to 1:5, preferably, the ratio of composition a) and b) in the range of 1:3 to 1:4.

In another aspect of the invention, the invention relates to the use of obtained catalyst according to the invention for the production process of δ-lactone from carbon dioxide and 1,3-butadiene in organic solvent.

In one embodiment, the production process of δ-lactone from carbon dioxide and 1,3-butadiene in organic solvent comprising: step i) adding of the catalyst according to the invention, carbon dioxide, and 1,3-butadiene into reactor filled with organic solvent, wherein the mole ratio of carbon dioxide to 1,3-butadiene is in the range of 1:1 to 1:3 and the mole ratio of the palladium catalyst to the 1,3-butadiene precursor is in the range of 1:1,000 to 1:3,000; and ii) heating the reactor at the temperature in the range of 60-120° C. for 1-10 hours.

Preferably, the production process of δ-lactone from carbon dioxide and 1,3-butadiene in organic solvent comprising: step i) adding of the catalyst according to the invention, carbon dioxide, and 1,3-butadiene into reactor filled with organic solvent, wherein the mole ratio of carbon dioxide to 1,3-butadiene is in the range of 1.2:1 to 1.5:1 and the mole ratio of the palladium catalyst to the 1,3-butadiene precursor is in the range of 1:1,500 to 1:1,700; and ii) heating the reactor at the temperature in the range of 70-80° C. for 3-4 hours.

In each step of the production of δ-lactone according to this invention, unless stated specifically, the organic solvents can be selected are, but not limited to acetonitrile, ethylene carbonate, propylene carbonate, pyridine, benzene, dimethyl formamide, dimethyl sulfoxide, or mixture thereof. Preferably, the solvent is selected from acetonitrile, ethylene carbonate, or mixture thereof.

The production process of δ-lactone according to this invention may further comprising the drying step if necessary, in which said step may be selected from, but not limited to stirring evaporation, vacuum drying, etc.

In one aspect, the production process of δ-lactone according to this invention may be operated in reactor, but not limited to fixed-bed reactor. The operation may be done in batch or continuous.

The following is an example which is only one embodiment of this invention and not intended to be limitation of this invention in any way.

Example 1: The Synthesis of Palladium Complex Catalyst

The Synthesis of Catalyst 1 (CAT 1)

About 15 mL of salicylaldehyde in ethanol (7.0% w/v) was added into the solution of palladium chloride ($PdCl_2$) in hydrochloric acid (1.7% w/v), wherein the reaction mole ratio of palladium chloride to salicylaldehyde was 1:2. with sodium acetate to 5-6 and stirred for 20 minutes. The obtained substance was filtered and washed with ethanol. The yellow-green solid was obtained as the catalyst 1.

The Synthesis of Catalyst 2 (CAT 2)

4 mL of 4,6-dimethoxy salicylaldehyde in acetone (4.2% w/v) was added into the solution of palladium chloride ($PdCl_2$) in hydrochloric acid (0.75 molar), wherein the reaction mole ratio of palladium chloride to 4,6-dimethoxy salicylaldehyde was 1:1.75. After being stirred for 15 minutes, the pH of said mixture was adjusted with sodium hydroxide (2 molar) until pH 7.5 was obtained. After adjusting pH, the mixture was stirred overnight. The obtained substance was filtered and washed with acetone. The dark yellow solid was obtained as the catalyst 2.

The Synthesis of Catalyst 3 (CAT 3)

About 0.2-0.25 g of 4-diethylamino salicylaldehyde in about 8 mL of the mixture of distilled water and acetone with the ratio of 1:3 was added into 0.6 mL of 3 molar palladium chloride ($PdCl_2$) in hydrochloric acid, wherein the reaction mole ratio of palladium chloride to 4-diethylamino salicylaldehyde was 1:2. After being stirred for 60 minutes, the pH of said mixture was adjusted with sodium hydroxide (2 molar) until pH 7.5 was obtained. After adjusting pH, the mixture was stirred overnight. The obtained substance was filtered and washed with acetone. The dark yellow solid was obtained as the catalyst 3.

The Synthesis of Catalyst 4 (CAT 4)

4 mL of 4-dibutylamino salicylaldehyde in acetone (5.6% w/v) was added into palladium chloride ($PdCl_2$) in hydrochloric acid (0.75 molar), wherein the reaction mole ratio of palladium chloride to 4-dibutylamino salicylaldehyde was 1:2. After being stirred for 15 minutes, the pH of said mixture was adjusted with sodium hydroxide (2 molar) until pH 7.5 was obtained. After adjusting pH, the mixture was stirred overnight. The obtained substance was filtered and washed with acetone. The dark yellow solid was obtained as the catalyst 4.

The Synthesis of Catalyst 5 (CAT 5)

5 mL of 5-chloro salicylaldehyde in acetone (3.5% w/v) was added into palladium chloride ($PdCl_2$) in hydrochloric acid (1.2 molar), wherein the reaction mole ratio of palladium chloride to 5-chloro salicylaldehyde was 1:2. After being stirred for 15 minutes, the pH of said mixture was adjusted with sodium hydroxide (2 molar) until pH 7.5 was obtained. After adjusting pH, the mixture was stirred overnight. The obtained substance was filtered and washed with acetone. The dark yellow solid was obtained as the catalyst 5.

The Synthesis of Catalyst 6 (CAT 6)

4 mL of 3,5-dichloro salicylaldehyde in acetone (4.4% w/v) was added into palladium chloride ($PdCl_2$) solution in hydrochloric acid (0.75 molar), wherein the reaction mole ratio of palladium chloride to 3,5-dichloro salicylaldehyde was 1:2. After being stirred for 15 minutes, the pH of said mixture was adjusted with sodium hydroxide (2 molar) until pH 7.5 was obtained. After adjusting pH, the mixture was stirred overnight. The obtained substance was filtered and washed with acetone. The dark yellow solid was obtained as the catalyst 6.

Example 2: The Preparation of δ-Lactone Compound

The catalysts 1 to 6 (CAT 1 to CAT 6) were tested for their catalytic efficacies to produce δ-lactone from the reaction of carbon dioxide and 1,3-butadiene compared to palladium acetylacetonate (Pd(acac)$_2$) as a reference catalyst (REF CAT). The test was performed according to the following process.

About 15-30 milligrams of catalysts, 40-50 milligrams of phosphorous compound, and about 7.5 grams of ethylene carbonate were added into the reactor. Then, 4 grams of each 1,3-butadiene and carbon dioxide were condensed into the reactor at reduced temperature by liquid nitrogen. The reactor was heated at 80° C. for 4 hours. After reaction was completed, the temperature of the reactor was reduced to room temperature. The residual precursor was removed by vacuum evaporation. The yellow mixed solution of δ-lactone product was obtained and identified by gas chromatography.

The Structure of the Catalyst According to the Invention

The structures of the synthesized catalysts CAT 1 to CAT 6 are shown in table 1.

TABLE 1

The structures of the catalyst according to the invention

| Sample | Structure |
|---|---|
| CAT 1 | 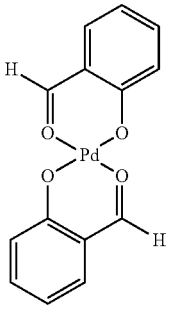 |
| CAT 2 | 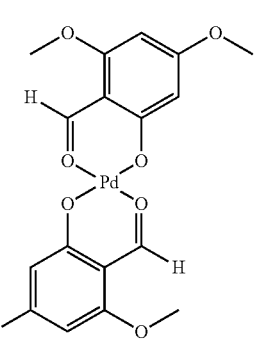 |
| CAT 3 | 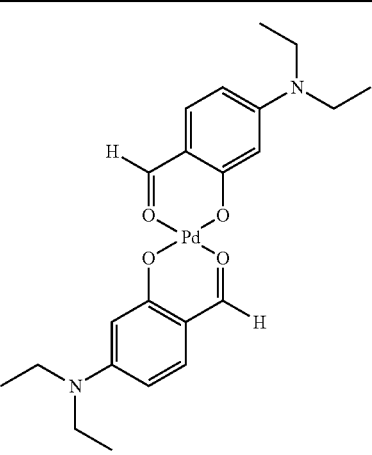 |
| CAT 4 | 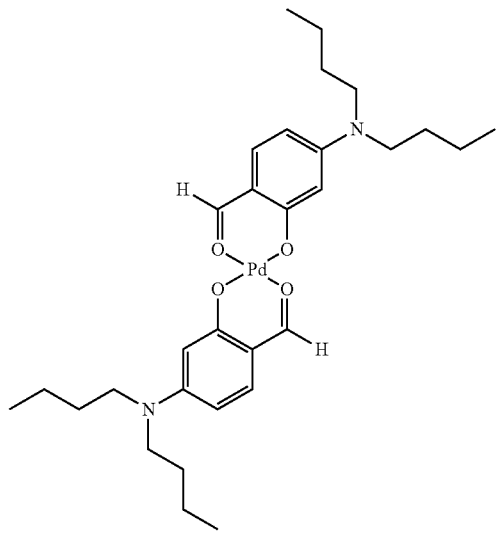 |
| CAT 5 | 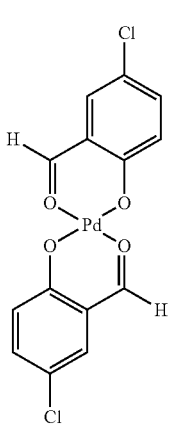 |

TABLE 1-continued

The structures of the catalyst according to the invention

| Sample | Structure |
| --- | --- |
| CAT 6 | (structure shown below) |

(structure: Pd complex with two 3,5-dichlorosalicylaldehyde ligands)

The Formation of δ-Lactone Compound

The catalytic efficacies for the production of δ-lactone from the reaction between carbon dioxide and 1,3-butadiene of the catalysts CAT 1 to CAT 6 compared to the reference catalyst (Pd(acac)$_2$) are shown in table 2.

TABLE 2

The catalytic efficacies for the production of δ-lactone of the catalysts according to the invention

| Catalytic System | | Produced d-lactone |
| --- | --- | --- |
| Palladium Complex Catalyst | Type of Phosphorous Compound | percentage (% yield δ-lactone) |
| REF CAT (Pd(acac)$_2$) | PPh$_3$ | 34 |
| REF CAT (Pd(acac)$_2$) | P(2-OMePh)$_3$ | 21 |
| REF CAT (Pd(acac)$_2$) | P(4-OMePh)$_3$ | 30 |
| CAT 1 | PPh$_3$ | 42 |
| CAT 1 | PCy$_3$ | 7.7 |
| CAT 1 | P(2-OMePh)$_3$ | 36 |
| CAT 1 | P(4-OMePh)$_3$ | 29 |
| CAT 2 | PPh$_3$ | 30 |
| CAT 3 | PPh$_3$ | 45 |
| CAT 4 | PPh$_3$ | 34 |
| CAT 5 | PPh$_3$ | 26 |
| CAT 6 | PPh$_3$ | 56 |

BEST MODE OF THE INVENTION

Best mode of the invention is as provided in the description of the invention.

The invention claimed is:

1. A catalyst composition for a production process of δ-lactone from carbon dioxide and 1,3-butadiene, wherein said catalyst composition comprising:

a) palladium metal complexes as shown in structure (I)

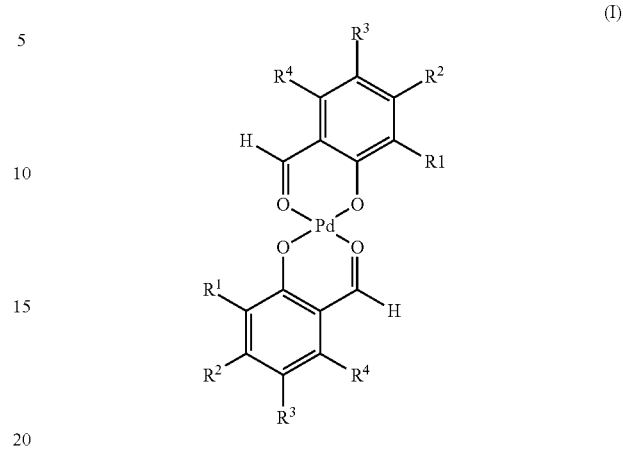

(I)

wherein, $R^1$, $R^2$, $R^3$ and $R^4$ independently represents a group selected from a hydrogen atom, a halogen atom, an alkyl group, an alkoxy group, an amine group, or optionally an alkenyl group, an alkynyl group, a phenyl group, a benzyl group, or a cyclic hydrocarbon group comprising a hetero atom; and b) phosphorus compound selected from a phosphine group having a general formula PR$_3^5$, wherein $R^5$ is selected from an alkyl group, a cycloalkyl group, or an aryl group.

2. The catalyst composition for the production process of δ-lactone from carbon dioxide and 1,3-butadiene according to claim 1, wherein the palladium metal complexes in a), $R^1$, $R^2$, $R^3$ and $R^4$ independently represents a group selected from a hydrogen atom, a halogen atom, an alkyl group having 1-4 carbon atoms, an alkoxy group having 1-4 carbon atoms, or a secondary amine having a general formula NR$_2^6$, wherein $R^6$ is an alkyl group having 1-4 carbon atoms.

3. The catalyst composition for the production process of δ-lactone from carbon dioxide and 1,3-butadiene according to claim 1 or 2, wherein the palladium metal complexes in a) is selected from palladium (II) salicylaldehyde, palladium (II) methoxy salicylaldehyde, palladium (II) 4-methoxy salicylaldehyde, palladium (II) 5-methoxy salicylaldehyde, palladium (II) 4,6-dimethoxy salicylaldehyde, palladium (II) 4-diethylamino salicylaldehyde, palladium (II) 4-dibutylamino salicylaldehyde, palladium (II) 5-bromo salicylaldehyde, palladium (II) 5-chloro salicylaldehyde, palladium (II) 3,5-dichloro salicylaldehyde, palladium (II) 3-methyl salicylaldehyde, palladium (II) 4-methyl salicylaldehyde, and palladium (II) 5-methyl salicylaldehyde.

4. The catalyst composition for the production process of δ-lactone from carbon dioxide and 1,3-butadiene according to claim 3, wherein the palladium metal complexes in a) is selected from palladium (II) salicylaldehyde, palladium (II) 4,6-dimethoxy salicylaldehyde, palladium (II) 4-diethylamino salicylaldehyde, palladium (II) 4-dibutylamino salicylaldehyde, palladium (II) 5-chloro salicylaldehyde, and palladium (II) 3,5-dichloro salicylaldehyde.

5. The catalyst composition for the production process of δ-lactone from carbon dioxide and 1,3-butadiene according to claim 1, wherein the phosphorus compound in b) is selected from triphenylphosphine, tricyclohexylphosphine, tris(2-methoxyphenyl)phosphine, tris(4-methoxyphenyl)phosphine, or a mixture thereof.

6. The catalyst composition for the production process of δ-lactone from carbon dioxide and 1,3-butadiene according to claim 5, wherein the phosphorus compound in b) is triphenylphosphine.

7. The catalyst composition for the production process δ-lactone from carbon dioxide and 1,3-butadiene according to any one of claims 1-6, wherein the ratio of the composition a) and b) is in a range of 1:1 to 1:5.

8. The catalyst composition for the production process of δ-lactone from carbon dioxide and 1,3-butadiene according to claim 7, wherein the ratio of the composition a) and b) is in the range of 1:3 to 1:4.

9. A production process for producing δ-lactone, comprising the step of reacting carbon dioxide and 1,3-butadiene in an organic solvent using the catalyst composition of claim 1.

10. The production process of δ-lactone according to claim 9, wherein the palladium metal complexes in a), $R^1$, $R^2$, $R^3$ and $R^4$ independently represents a group selected from a hydrogen atom, a halogen atom, an alkyl group having 1-4 carbon atoms, an alkoxy group having 1-4 carbon atoms, or a secondary amine having a general formula $NR_2^6$, wherein $R^6$ is an alkyl group having 1-4 carbon atoms.

11. The production process of δ-lactone according to claim 9 or 10, wherein the palladium metal complexes in a) is selected from palladium (II) salicylaldehyde, palladium (II) methoxy salicylaldehyde, palladium (II) 4-methoxy salicylaldehyde, palladium (II) 5-methoxy salicylaldehyde, palladium (II) 4,6-dimethoxy salicylaldehyde, palladium (II) 4-diethylamino salicylaldehyde, palladium (II) 4-dibutylamino salicylaldehyde, palladium (II) 5-bromo salicylaldehyde, palladium (II) 5-chloro salicylaldehyde, palladium (II) 3,5-dichloro salicylaldehyde, palladium (II) 3-methyl salicylaldehyde, palladium (II) 4-methyl salicylaldehyde, and palladium (II) 5-methyl salicylaldehyde.

12. The production process of δ-lactone according to claim 11, wherein the palladium metal complexes in a) is selected from palladium (II) salicylaldehyde, palladium (II) 4,6-dimethoxy salicylaldehyde, palladium (II) 4-diethylamino salicylaldehyde, palladium (II) 4-dibutylamino salicylaldehyde, palladium (II) 5-chloro salicylaldehyde, and palladium (II) 3,5-dichloro salicylaldehyde.

13. The production process of δ-lactone according to claim 9, wherein the phosphorus compound in b) is selected from triphenylphosphine, tricyclohexylphosphine, tris(2-methoxyphenyl)phosphine, tris(4-methoxyphenyl)phosphine), or a mixture thereof.

14. The production process of δ-lactone according to claim 13, wherein the phosphorus compound in b) is triphenylphosphine.

15. The production process of δ-lactone according to any one of claims 9-14, wherein the ratio of composition a) and b) is in the range of 1:1 to 1:5.

16. The production process of δ-lactone according to claim 15, wherein the ratio of composition a) and b) is in the range of 1:3 to 1:4.

\* \* \* \* \*